United States Patent
Tahtaoui

(10) Patent No.: US 10,537,549 B2
(45) Date of Patent: Jan. 21, 2020

(54) DIHYDROISOXAZOLE COMPOUND FOR USE IN CONTROLLING SEA LICE

(71) Applicant: Elanco Tiergesundheit AG, Basel (SZ)

(72) Inventor: Chouaib Tahtaoui, Rixheim (FR)

(73) Assignee: Elanco Tiergesundheit AG, Basel (CH)

( * ) Notice: Subject to any disclaimer, the term of this patent is extended or adjusted under 35 U.S.C. 154(b) by 0 days.

(21) Appl. No.: 16/099,590

(22) PCT Filed: May 3, 2017

(86) PCT No.: PCT/US2017/030825
§ 371 (c)(1),
(2) Date: Nov. 7, 2018

(87) PCT Pub. No.: WO2017/196607
PCT Pub. Date: Nov. 16, 2017

(65) Prior Publication Data
US 2019/0142795 A1    May 16, 2019

Related U.S. Application Data

(60) Provisional application No. 62/333,993, filed on May 10, 2016.

(51) Int. Cl.
| | | |
|---|---|---|
| *A61K 31/381* | (2006.01) | |
| *A23K 50/80* | (2016.01) | |
| *A23K 20/137* | (2016.01) | |
| *A01N 43/80* | (2006.01) | |

(52) U.S. Cl.
CPC ............ *A61K 31/381* (2013.01); *A01N 43/80* (2013.01); *A23K 20/137* (2016.05); *A23K 50/80* (2016.05)

(58) Field of Classification Search
None
See application file for complete search history.

(56) References Cited

U.S. PATENT DOCUMENTS

| | | | |
|---|---|---|---|
| 8,377,942 B2 | 2/2013 | Nanchen et al. | |
| 8,592,418 B2 | 11/2013 | Nanchen et al. | |
| 8,648,081 B2 * | 2/2014 | An ......................... | A01N 43/80 |
| | | | 514/254.04 |
| 9,044,389 B2 | 6/2015 | Nanchen et al. | |

FOREIGN PATENT DOCUMENTS

| | | |
|---|---|---|
| WO | 2010070068 A2 | 6/2010 |
| WO | 2011157733 A2 | 12/2011 |
| WO | 2012017359 A1 | 2/2012 |
| WO | 2012158396 A1 | 11/2012 |
| WO | 2014090918 A1 | 6/2014 |
| WO | 2016077158 A1 | 5/2016 |

OTHER PUBLICATIONS

P. Stahl, et al., Handbook of Pharmaceutical Salts: Properties, Selection and Use, (VCHA/Wiley-VCH, 2002).
S.M. Berge, et al., "Pharmaceutical Salts," Journal of 25 Pharmaceutical Sciences, vol. 66, No. 1, Jan. 1977.
Patent Cooperation Treaty International Search Report and the Written Opinion of the International Searching Authority pertaining to International Application No. PCT/2017/030825; dated Jun. 29, 2017.

* cited by examiner

*Primary Examiner* — Kamal A Saeed
(74) *Attorney, Agent, or Firm* — Joseph Matthew Pletcher

(57) ABSTRACT

The present invention provides a dihydroisoxazole of formula: or a salt thereof, for use in the control of sea lice in fish.

(I)

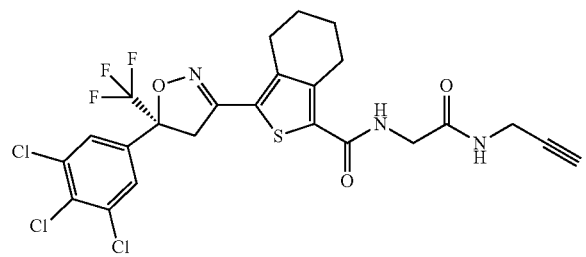

5 Claims, No Drawings

DIHYDROISOXAZOLE COMPOUND FOR USE IN CONTROLLING SEA LICE

The present invention relates to a particular dihydroisoxazole compound for use in the control of sea lice. The present invention further relates to a method of controlling sea lice by administering a veterinary effective amount of the particular dihydroisoxazole compound.

Sea lice are ectoparasites which feed on the mucus, epidermal tissue and blood of host marine fish, in particular salmon. Sea lice belong to the sub-class of copepods. Sea lice can cause significant harm to host fish, in particular they can cause serious fin damage, skin erosion, bleeding and open wounds. Additionally, sea lice can cause chronic stress response in fish, which in turn can make them susceptible to other diseases. Sea lice infestations are a major problem in salmon farming and can result in significant economic loss. There are a number of treatments already on the market for controlling sea-lice including bath treatments, such as organophosphates (for example, dichlorvos and azamethiphos) and pyrethroids (for example, cypermethrin and deltamethrin), and in-feed-treatments, such as avermectins (for example, ivermectin and emamectin benzoate) and growth regulators (for example, teflubenzuron). However, resistance to many of these treatments has been observed and therefore, there remains a need for new treatments. In particular, there is a need for new treatments having a long duration of action.

WO2012/158396 discloses certain dihydroisoxazole compounds which are described as being useful in controlling parasite infestations, including both ectoparasite, in particular tick, and endoparasite infestations. The specific compounds disclosed include the racemic compound N-(2-oxo-2-(prop-2-ynylamino)ethyl)-3-(5-(3,4,5-trichlorophenyl)-5-(trifluoromethyl)-4,5-dihydroisoxazol-3-yl)-4,5,6,7-tetrahydrobenzo[c]thiophene-1-carboxamide (Example 47).

It has surprisingly been found that the particular dihydroisoxazole compound N-[2-oxo-2-(prop-2-ynylamino)ethyl]-3-[(5S)-5-(3,4,5-trichlorophenyl)-5-(trifluoromethyl)-4H-isoxazol-3-yl]-4,5,6,7-tetrahydro-2-benzothiophene-1-carboxamide is effective against sea lice in fish.

The present invention provides a compound of formula (I):

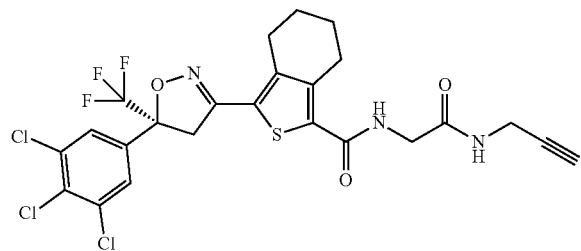

(I)

or a salt thereof, for use in the control of sea lice in fish.

The present invention further provides a method of controlling sea lice in fish comprising administering to the fish a veterinary effective amount of a compound of formula (I), or a salt thereof.

The present invention further provides the use of a compound of formula (I), or a salt thereof, for the manufacture of a veterinary composition for controlling sea lice in fish.

The present invention further provides a composition comprising a compound of formula (I), or a salt thereof, for controlling sea lice in fish.

In an embodiment of the present invention, the fish are salmonids.

In another embodiment of the present invention, the compound of formula (I) is orally administered.

The present invention further provides a fish feed pre-mix composition comprising a compound of formula (I), or a salt thereof.

The present invention further provides a medicated fish feed comprising a compound of formula (I), or a salt thereof.

As used herein, the term "controlling" refers to reducing the number of sea lice, eliminating sea lice and/or preventing further sea lice infestation.

As used herein, the term "sea lice" refers to all members of the family Caligidae. In particular, it includes *Lepeophtheirus salmonis, Caligus rogercresseyi* and *Caligus clemensi.*

As used herein, the term "salmonids" refers to all fish in the family Salmonidae. In particular, it includes Atlantic Salmon (*Salmo salar*) and Pacific Salmon.

As used herein, the term "veterinary effective amount" refers to the amount or dose of the compound of formula (I), or a salt thereof, which, upon single or multiple dose administration to the fish, provides the desired effect.

An effective amount can be readily determined by one skilled in the art by the use of known techniques and by observing results obtained under analogous circumstances. In determining the veterinary effective amount a number of factors are considered, including, but not limited to: the species of fish; the degree of sea lice infestation; the response of the fish population; the mode of administration; the bioavailability characteristics of the preparation administered; the dose regimen selected; the use of concomitant medication; and other relevant circumstances.

The compound of formula (I), or a salt thereof, may be administered to the fish by any route which has the desired effect including, but not limited to oral administration or administration in the form of a bath treatment. Oral administration is preferred. More particularly, in-feed administration is preferred. In one embodiment of the present invention, the compound of formula (I), or a salt thereof, is orally administered at a daily dose of between 1 and 10 mg/kg of fish biomass, preferably at a daily dose of between 3 and 7 mg/kg of fish biomass and most preferably at a daily dose of about 5 mg/kg of fish biomass.

In one embodiment of the present invention, the compound of formula (I), or a salt thereof, is administered at the end of the fresh water stage or at the beginning of the sea water stage in the farming of the fish. In one embodiment, the overall treatment period during which the compound of formula (I), or a salt thereof, is administered is 3 to 14 days, preferably 5 to 14 days, more preferably 5 to 10 days and most preferably 7 days. During the overall treatment period, the compound of formula (I), or a salt thereof, may be administered, for example, daily or once every two days. Preferably, it is administered daily. In a preferred embodiment, administration is daily for a period of 7 days.

In a preferred embodiment, the compound of formula (I), or a salt thereof, is orally administered at a daily dose of between 1 and 10 mg/kg of fish biomass for a period of 3 to 14 days. In another preferred embodiment, the compound of formula (I), or a salt thereof, is orally administered at a daily dose of between 3 and 7 mg/kg of fish biomass for a period of 5 to 10 days. In a more preferred embodiment, the compound of formula (I), or a salt thereof, is orally administered at a daily dose of about 5 mg/kg of fish biomass for a period of 7 days.

In one embodiment of the present invention, the compound of formula (I), or a salt thereof, is administered in a medicated fish feed. Fish feed is typically in the form of granules or pellets. Common ingredients of said fish feed granules or pellets include fishmeal, fish oil, vegetable proteins, saccharides and polysaccharides (including mannans, glucans and alginates). In addition, excipients such as pigments, vitamins, minerals and binders may also be included. The compound of formula (I), or a salt thereof, may be incorporated into the feed prior to pelleting or alternatively, the compound of formula (I), or a salt thereof, may be coated onto the granules or pellets, either on its own or in the form of a pre-mix. The pre-mix may contain, in addition to the active compound, one or more veterinary acceptable excipients such as starch, fumed silica, microcrystalline cellulose, lactose and a preservative.

In one embodiment of the present invention, the amount of the compound of formula (I), or a salt thereof, present in the fish feed pre-mix composition is between 5 and 20% (w/w), preferably between 10 and 15% (w/w) and most preferably about 12.5% (w/w), based in each case on the entire weight of the pre-mix.

In another embodiment of the present invention, the amount of the compound of formula (I), or a salt thereof, present in the medicated fish feed is between 0.01 and 2% (w/w), preferably between 0.1 and 1% (w/w) and more preferably about 0.5% (w/w), based in each case on the entire weight of the fish feed.

Salts of the compounds of the invention, including pharmaceutically acceptable salts, and common methodology for preparing them, are known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977.

The compound of formula (I) can be prepared by one of ordinary skill in the art following art recognized techniques and procedures. More specifically, compound of formula (I) can be prepared as set forth in the preparations and example set forth below.

The reagents and starting materials are readily available to one of ordinary skill in the art.

PREPARATION 1

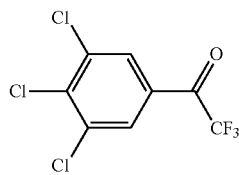 [SMILES: O=C(c1cc(Cl)c(Cl)c(Cl)c1)C(F)(F)F]

2,2,2-trifluoro-1-(3,4,5-trichlorophenyl)ethanone

Add iso-propyl magnesium chloride (2 M, 230.47 mL) dropwise to a solution of 5-bromo-1,2,3-trichloro-benzene (100.00 g, 384.11 mmol) in tetrahydrofuran (1 L) under $N_2$ atmosphere at 0° C. and then stir the mixture at 0° C. for 2 hours. Cool the mixture to −5° C. and add ethyl 2,2,2-trifluoroacetate (109.15 g, 768.22 mmol) dropwise. Then stir the mixture at 25° C. for 14 hours, quench with aqueous ammonium chloride (1 L) and extract organic materials with ethyl acetate (1 L×3). Dry the organic layer over sodium sulfate, filter and concentrate under reduced pressure to dryness. Distill the residue to afford 2,2,2-trifluoro-1-(3,4,5-trichlorophenyl)ethanone at 86° C. under −0.05 MPa in 74% yield (175.00 g) as off-white solid. $^1$H NMR (CDCl$_3$) δ 8.05 (s, 2H).

PREPARATION 2

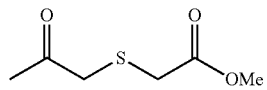

Methyl 2-acetonylsulfanylacetate

Add methyl 2-sulfanylacetate (200 g, 1.88 mol, 170.94 mL) to an ice-cold solution of sodium methoxide, prepared from sodium (44.09 g, 1.92 mol, 45.45 mL) and methanol (860 mL) under nitrogen gas, followed by 1-chloropropan-2-one (183 g, 1.98 mol) over a period of 30 min. Stir the resulting mixture at 0 to 25° C. for 30 min and then at 50 to 60° C. for an additional 30 min. Filter the reaction mixture to remove the precipitates (sodium chloride). After removal of the solvent, pour the residue into cold water and then extract with ethyl acetate (300 mL×2). Wash the extract with brine (100 mL), dry with sodium sulfate and concentrate to give a crude material. Distill the crude material at a reduced pressure to afford methyl 2-acetonylsulfanylacetate (250 g, 82% yield) as yellow oil.
$^1$H NMR (CDCl$_3$) δ 3.70 (s, 3H), 3.40 (s, 2H), 3.24 (s, 2H), 2.26 (s, 3H).

PREPARATION 3

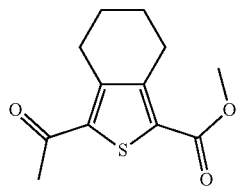 [SMILES: COC(=O)c1sc(C(C)=O)c2c1CCCC2]

Methyl 3-acetyl-4,5,6,7-tetrahydro-2-benzothiophene-1-carboxylate

Add methyl 2-acetonylsulfanylacetate (50.00 g, 308.24 mmol) to a solution of sodium methoxide (34.69 g, 642.17 mmol) in methanol (500.00 mL) cooled to 0° C. under nitrogen gas followed by cyclohexane-1,2-dione (25.92 g, 231.18 mmol) over a period of 15 min at 0° C. Stir the resulting mixture at 0° C. to 25° C. for 45 min. After the temperature is reached to 10° C., solid is precipitated out. Filter the reaction mixture. Wash the filter cake with methanol (50 mL) dried under vacuum to give compound methyl 3-acetyl-4,5,6,7-tetrahydro-2-benzothiophene-1-carboxylate (127 g, 42% yield) as yellow solid. $^1$H NMR (CDCl$_3$) δ 3.89 (s, 3H), 3.10-2.90 (m, 2H), 2.53 (s, 3H), 1.80-1.60 (m, 3H).

PREPARATION 4

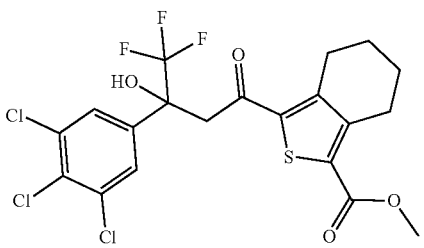 [SMILES: COC(=O)c1sc(C(=O)CC(O)(c2cc(Cl)c(Cl)c(Cl)c2)C(F)(F)F)c2c1CCCC2]

Methyl 3-[4,4,4-trifluoro-3-hydroxy-3-(3,4,5-trichlorophenyl)butanoyl]-4,5,6,7-tetrahydro-2-benzothiophene-1-carboxylate Add lithium bis(trimethylsilyl)amide (1 M, 272.77 mL) to a solution of methyl 3-acetyl-4,5,6,7-tetrahydro-2-benzothiophene-1-carboxylate (50.00 g, 209.82 mmol) in tetrahydrofuran (2.5 L) dropwise under nitrogen gas atmosphere at −78° C. and then stir the mixture at −30° C. for 2 hours. Cool the mixture to −78° C. and add 2,2,2-trifluoro-1-(3,4,5-trichlorophenyl)ethanone (69.86 g, 251.78 mmol). Stir the mixture at −30° C. for 2 hours. Use thin layer chromatography (petroleum ether:ethyl acetate=10:1, $R_f$=0.4) to show the reaction progress. Quench the mixture with saturated aqueous ammonium chloride (1 L) and extract with ethyl acetate (1 L×3). Dry the organic layer over sodium sulfate, filter and concentrate under reduced pressure to dryness. Recrystallize the residue in hexane (500 mL) and filter. Wash the solid with hexanes (200 mL), dry under reduced pressure to afford methyl 3-[4,4,4-trifluoro-3-hydroxy-3-(3,4,5-trichlorophenyl)butanoyl]-4,5,6,7-tetrahydro-2-benzothiophene-1-carboxylate (100.00 g, 83% yield) as off-white solid. $^1$H NMR (CDCl$_3$) δ 7.64 (s, 2H), 5.93 (s, 1H), 3.93 (s, 3H), 3.63 (d, J=16.8 Hz, 1H), 3.52 (d, J=16.8 Hz, 1H), 3.10-3.00 (m, 2H), 2.95-2.85 (m, 2H), 1.80-1.65 (m, 4H).

PREPARATION 5

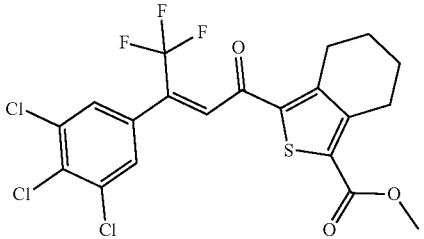 [SMILES: COC(=O)c1sc(C(=O)/C=C(/c2cc(Cl)c(Cl)c(Cl)c2)C(F)(F)F)c2c1CCCC2]

Methyl 3-[(Z)-4,4,4-trifluoro-3-(3,4,5-trichlorophenyl)but-2-enoyl]-4,5,6,7-tetrahydro-2-benzothiophene-1-carboxylate Add thionyl chloride (34.60 g, 290.83 mmol) to a mixture of methyl 3-[4,4,4-trifluoro-3-hydroxy-3-(3,4,5-trichlorophenyl)butanoyl]-4,5,6,7-tetrahydro-2-benzothiophene-1-carboxylate (100.00 g, 193.89 mmol) and pyridine (61.35 g, 775.55 mmol) in dichloromethane (500 mL) dropwise at 0° C. and then stir the mixture at 25° C. for 2 hours. Use thin layer chromatography (petroleum ether:ethyl acetate=10:1, $R_f$=0.57 and 0.50) to show the reaction progress. Quench the mixture with water (50 mL) and extract with dichloromethane (50 mL×3). Wash the organic layer with aqueous sodium bicarbonate (50 mL), dry over sodium sulfate, filter and concentrate under reduced pressure to dryness to afford methyl 3-[(Z)-4,4,4-trifluoro-3-(3,4,5-trichlorophenyl)but-2-enoyl]-4,5,6,7-tetrahydro-2-benzothiophene-1-carboxylate (80.00 g, 83% yield) as pale yellow solid. $^1$H NMR (CDCl$_3$, 400 MHz) δ 7.54 (s, 0.37H), 7.33 (s, 1.54 H), 7.26 (s, 1H), 3.91 (s, 3H), 3.10-2.90 (m, 4H), 1.80-1.60 (m, 4 H).

PREPARATION 6

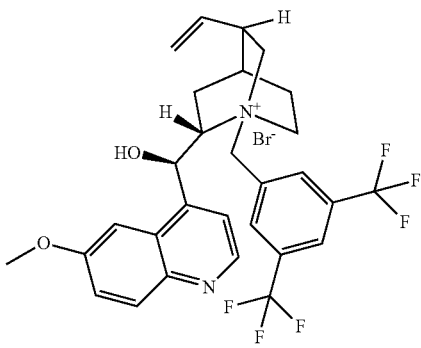 [SMILES: C=CC1C[N+]2(Cc3cc(C(F)(F)F)cc(C(F)(F)F)c3)CCC1C[C@H]2[C@H](O)c1ccnc2ccc(OC)cc12 ; [Br-]]

(1S,2S,4S,5R)-1-(3,5-bis(trifluoromethyl)benzyl)-2-((R)-hydroxy(6-methoxyquinolin-4-yl)methyl)-5-vinylquinuclidin-1-ium bromide Stir a mixture of (R)-(6-methoxy-4-quinolyl)-[(2S)-5-vinylquinuclidin-2-yl]methanol (30.00 g, 92.47 mmol) and 1-(bromomethyl)-3,5-bis(trifluoromethyl)benzene (34.07 g, 110.96 mmol) in acetone (500 mL) at 50° C. for 16 hours. Use thin layer chromatography (ethyl acetate, $R_f$=0.15) to show the consumption of starting material. Concentrate the mixture under reduced pressure to dryness. Recrystallize the residue from tetrahydrofuran (300 mL) and filter. Wash the solid with tetrahydrofuran (300 mL), dissolve in dichloromethane (300 mL) and toluene (150 mL) and then concentrate under reduced pressure to dryness. (1S,2S,4S,5R)-1-(3,5-bis(trifluoromethyl)benzyl)-2-((R)-hydroxy(6-methoxyquinolin-4-yl)methyl)-5-vinylquinuclidin-1-ium bromide (50.00 g, 77% yield) is obtained as pale yellow solid. $^1$H NMR (DMSO-d$_6$, 400 MHz) δ 8.83 (d, J=4.0 Hz, 1H), 8.47 (s, 2H), 8.39 (s, 1H), 8.05 (d, J=9.2 Hz, 1H), 7.76 (d, J=4.4 Hz, 1H), 7.54 (dd, J=9.2 Hz, 2.4 Hz, 1H), 7.39 (d, J=2.4 Hz, 1H), 6.90 (d, J=4.0 Hz, 1H), 6.52 (d, J=3.2 Hz, 1H), 5.80-5.60 (m, 1H), 5.55 (d, J=12.4 Hz, 1H), 5.13 (d, J=17.6 Hz, 1H), 5.03 (d, J=10.6 Hz, 1H), 4.95 (d, J=12.4 Hz, 1H), 4.40-4.30 (m, 1H), 4.02 (s, 3H), 3.85-3.75 (m, 1H), 3.75-3.65 (m, 1H), 3.45 (t, J=12.0 Hz, 1H), 3.30-3.20 (m, 1H), 2.70-2.60 (m, 1H), 2.30-2.20 (m, 1H), 2.20-2.10 (m, 1H), 2.05-1.95 (m, 1H), 1.85-1.75 (m, 1H), 1.49 (t, J=10.8 Hz, 1H).

PREPARATION 7

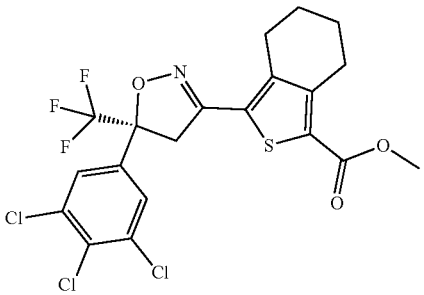 [SMILES: COC(=O)c1sc(C2=NO[C@@](c3cc(Cl)c(Cl)c(Cl)c3)(C(F)(F)F)C2)c2c1CCCC2]

Methyl 3-[(5S)-5-(3,4,5-trichlorophenyl)-5-(trifluoromethyl)-4H-isoxazol-3-yl]-4,5,6,7-tetrahydro-2-benzothiophene-1-carboxylate Add hydroxylamine (301.35 mmol, 50% purity) to a mixture of methyl 3-[(Z)-4,4,4-trifluoro-3-(3,4,5-trichlorophenyl)but-2-enoyl]-4,5,6,7-tetrahydro-2-benzothiophene-1-carboxylate (50.00 g, 100.45 mmol) and (1S,2S,4S,5R)-1-(3,5-bis(trifluoromethyl)benzyl)-2-((R)-hydroxy(6-methoxyquinolin-4-yl)methyl)-5-vinylquinuclidin-1-ium bromide (6.65 g, 11.05 mmol) in chloroform (1.50 L) dropwise at −15° C., follow by the addition of sodium hydroxide (10 M, 30.14 mL) dropwise at −15° C. Then stir the mixture at −15° C. for 2 hours. Use thin layer chromatography (petroleum ether:ethyl acetate=10:1, $R_f$=0.48) to show the reaction progress. Quench the mixture with hydrochloric acid (1 M) until pH=2 and extract with dichloromethane (1.5 L×3). Dry the organic layer over sodium sulfate, filter and concentrate under reduced pressure to dryness to afford methyl 3-[(5S)-5-(3,4,5-trichlorophenyl)-5-(trifluoromethyl)-4H-isoxazol-3-yl]-4,5,6,7-tetrahydro-2-benzothiophene-1-carboxylate (50.00 g, 87% yield) as off-white solid. $^1$H NMR (CDCl$_3$) δ 7.62 (s, 2H), 4.54 (d, J=17.2 Hz, 1H), 3.88 (s, 3H), 3.66 (d, J=17.2 Hz, 1H), 3.10-3.00 (m, 2H), 2.95-2.85 (m, 2H), 1.80-1.65 (m, 4H).

PREPARATION 8

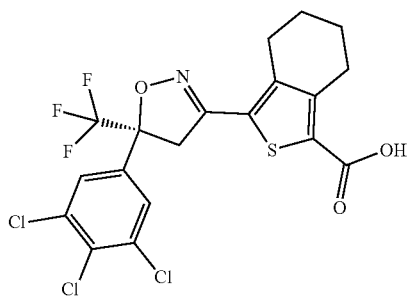 [SMILES: O=C(O)c1sc(C2=NO[C@@](c3cc(Cl)c(Cl)c(Cl)c3)(C(F)(F)F)C2)c2c1CCCC2]

3-[(5S)-5-(3,4,5-trichlorophenyl)-5-(trifluoromethyl)-4H-isoxazol-3-yl]-4,5,6,7-tetrahydro-2-benzothiophene-1-carboxylic acid Stir a mixture of methyl 3-[(5S)-5-(3,4,5-trichlorophenyl)-5-(trifluoromethyl)-4H-isoxazol-3-yl]-4,5,6,7-tetrahydro-2-benzothiophene-1-carboxylate (50.00 g, 97.51 mmol) and lithium hydroxide monohydrate (20.46 g, 487.55 mmol) in methanol (800 mL) and water (200 mL) at 25° C. for 12 hours. Use thin layer chromatography (petroleum ether:ethyl acetate=10:1, $R_f$=0.08) to show the consumption of starting material. Acidify the mixture by hydrochloric acid (1 M) until pH=2 and then extract with dichloromethane (1 L×3). Dry the organic layer over sodium sulfate, filter and concentrate under reduced pressure to dryness to afford 3-[(5S)-5-(3,4,5-trichlorophenyl)-5-(trifluoromethyl)-4H-isoxazol-3-yl]-4,5,6,7-tetrahydro-2-benzothiophene-1-carboxylic acid (46.00 g, 85% yield) as off-white solid. $^1$H NMR (DMSO-d$_6$) δ 7.87 (s, 2H), 4.40-4.20 (m, 2H), 3.00-2.90 (m, 2H), 2.85-2.75 (m, 2H), 1.70-1.55 (m, 4H).

Preparation 9

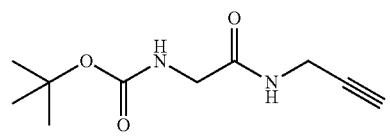

tert-butyl N-[2-oxo-2-(prop-2-ynylamino)ethyl]carbamate

Stir a mixture of 2-(tert-butoxycarbonylamino)acetic acid (30.00 g, 171.25 mmol), prop-2-yn-1-amine (10.38 g, 188.38 mmol), 1-[Bis(dimethylamino)methylene]-1H-1,2,3-triazolo[4,5-b]pyridinium 3-oxid hexafluorophosphate (78.14 g, 205.50 mmol) and N,N-diisopropylethylamine (66.40 g, 513.75 mmol) in dichloromethane (1.00 L) at 25° C. for 16 hours. Use thin layer chromatography (petroleum ether:ethyl acetate=1:1, $R_f$=0.26) to show the consumption of starting material. Dilute the mixture in water (1 L) and extract with dichloromethane (1 L×3). Dry the organic layer over sodium sulfate, filter and concentrate under reduced pressure to dryness. Purify the crude material by silica gel chromatography (petroleum ether:ethyl acetate=10:1 to 1:1) to afford tert-butyl N-[2-oxo-2-(prop-2-ynylamino)ethyl]carbamate (30.00 g, 74% yield) as off-white solid. $^1$H NMR (CDCl$_3$) δ 6.48 (brs, 1H), 5.18 (brs, 1H), 4.07 (dd, J=5.2 Hz, 2.4 Hz, 2H), 3.82 (d, J=5.6 Hz, 2H), 2.23 (t, J=2.4 Hz, 1H), 1.46 (s, 9H).

PREPARATION 10

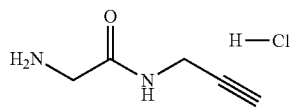

2-amino-N-prop-2-ynyl-acetamide hydrochloride

Stir a mixture of tert-butyl N-[2-oxo-2-(prop-2-ynylamino)ethyl]carbamate (7.00 g, 32.98 mmol) and hydrochloric acid/dioxane (4 M, 50 mL) in dioxane (50 mL) at 25° C. for 2 hours. Use thin layer chromatography (petroleum ether:ethyl acetate=1:1, $R_f$=0.04) to show the consumption of starting material. Concentrate the mixture under reduced pressure to dryness to afford crude 2-amino-N-prop-2-ynyl-acetamide hydrochloride (4.90 g) as off-white solid, which can be used in the next step directly without further purification. $^1$H NMR (DMSO-$d_6$) δ 8.87 (brs, 1H), 8.14 (brs, 3H), 3.93 (dd, J=5.6 Hz, 2.4 Hz, 2H), 3.53 (s, 2H), 3.18 (t, J=2.4 Hz, 1H).

EXAMPLE 1

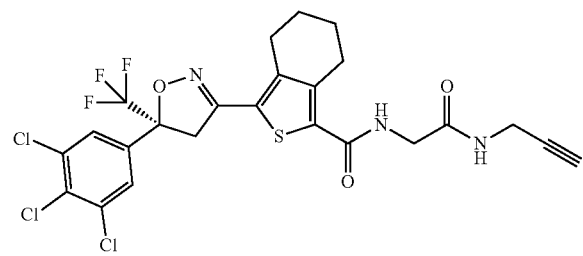 [SMILES: C#CCNC(=O)CNC(=O)c1sc(C2=NO[C@@](c3cc(Cl)c(Cl)c(Cl)c3)(C(F)(F)F)C2)c2c1CCCC2]

N-[2-oxo-2-(prop-2-ynylamino)ethyl]-3-[(5S)-5-(3,4,5-trichlorophenyl)-5-(trifluoromethyl)-4H-isoxazol-3-yl]-4,5,6,7-tetrahydro-2-benzothiophene-1-carboxamide Stir a mixture of 3-[(5S)-5-(3,4,5-trichlorophenyl)-5-(trifluoromethyl)-4H-isoxazol-3-yl]-4,5,6,7-tetrahydro-2-benzothiophene-1-carboxylic acid (15.00 g, 30.08 mmol), 2-amino-N-prop-2-ynyl-acetamide (4.90 g, 33.09 mmol, HCl), 1-[bis(dimethylamino)methylene]-1H-1,2,3-triazolo[4,5-b]pyridinium 3-oxid hexafluorophosphate (13.72 g, 36.10 mmol) and N,N-diisopropylethylamine (11.66 g, 90.24 mmol) in dichloromethane (500 mL) at 25° C. for 12 hours. Use thin layer chromatography (petroleum ether:ethyl acetate=3:1, $R_f$=0.30) to show the reaction progress. Dilute the mixture in water (500 mL) and extract with dichloromethane (500 mL×3). Wash the organic layer with brine (500 mL), dry over sodium sulfate, filter and concentrate under reduced pressure to dryness. Purify the crude material by silica gel chromatography (petroleum ether:ethyl acetate=10:1 to 1:1) to afford the corresponding product with 70% ee, which is further purified by supercritical fluid chromatography (SFC) to afford N-[2-oxo-2-(prop-2-ynylamino)ethyl]-3-[(5S)-5-(3,4,5-trichlorophenyl)-5-(trifluoromethyl)-4H-isoxazol-3-yl]-4,5,6,7-tetrahydro-2-benzothiophene-1-carboxamide (6.00 g, 34% yield, 99.8% ee) as off-white solid. $^1$H NMR (CDCl$_3$): δ 7.62 (s, 2H), 7.05-6.90 (m, 2H), 4.18 (d, J=4.8 Hz, 2H), 4.10 (t, J=2.4 Hz, 2H), 4.06 (d, J=16.8 Hz, 1H), 3.68 (d, J=16.8 Hz, 1H), 3.10-2.95 (m, 2H), 2.90-2.80 (m, 2H), 2.24 (t, J=2.4 Hz, 1H), 1.90-1.70 (m, 4H).
LC/MS (m/z): 592 (M+H)$^+$.
SFC conditions as follows
SFC analytical conditions:
Instrument: Berger SFC
Chiralcel OD-3 150×4.6 mm I.D., 3 um
Mobile phase: A: CO$_2$ B: ethanol (0.05% DEA)
Gradient: from 5% to 40% of B in 5.0 min and hold 40% for 2.5 min, then 5% of B for 2.5 min Flow rate: 2.5 mL/min
Wavelength: 220 nm
Column temperature: 35° C.
Retention time: 6.12 min (S-isomer)
SFC separation conditions:
Instrument: Thar SFC 200;
Column: AS 250 mm*50 mm, 10 um;
Mobile phase: A: Supercritical CO2, B: EtOH, Base-EtOH, Begin B: 40%, End B: 40%
Wavelength 220 nm
Flow rate 200 ml/min
Column Temp: 38° C.;
Nozzle Pressure: 100 Bar;
Nozzle Temp: 40° C.;
Evaporator Temp: 40° C.;
Trimmer Temp: 25° C.;
Retention time: 5.66 min (R-isomer), 5.96 min (S-isomer)

Activity In Vitro Against *Lepeophtheirus Salmonis* at Copepodid Stage

Sea lice copepodids are used to seed a 96-well plate containing the compound of Example 1 (test compound). The test compound is tested by serial dilution in order to determine its minimal effective dose (MED). Copepodids are left in contact with the test compound diluted in sea water for 1 hour. They are then incubated in untreated sea water for 48 h. Efficacy against sea lice is then confirmed if no copepodid moves over a period of 80 seconds.

In this test, the compound of Example 1 showed 100% efficacy at a dose of as low as 0.5 ng/ml sea water.

Activity In Vivo Against *Lepeophtheirus Salmonis* on Atlantic Salmon Using in-Feed Application 60 Salmon (Atlantic Salmon, *S. salar*) of average weight 306.5 g are treated with medicated pellets containing the compound of Example 1 (test compound) at a dose of 5 mg/kg/day during 7 consecutive days. The medicated pellets are prepared by dry coating commercially available fish feed pellets with pre-mix containing the test compound to reach a content of 0.5% (w/w) test compound in the fish feed, sealing with 1% fish oil and administering at a 1% feeding rate. The treatment is carried out in sea water. After treatment, the fish are challenged with copepodids (the MERL resistant strain IoA-01) on 35, 100 and 150 days post-treatment. During the study the water temperature varies between 7 and 10° C. Fish weight and sea louse numbers are assessed 42, 107 and 157 days post-treatment. Counts are conducted on 30 fish at each sampling occasion.

Efficacy is determined by comparison with a negative control (placebo) group.
Efficacy is calculated using the formula:

% Efficacy=100−(100×mean of treatment group/mean of control).

All fish are anaesthetized with 2-phenoxy-ethanol and examined for louse settlement under a dissecting microscope. After counting, fish are returned to the tanks.

In this test, the compound of Example 1 showed 100% efficacy on the challenge performed 35, 100 and 150 days post treatment.

I claimed:
1. A compound of the formula:

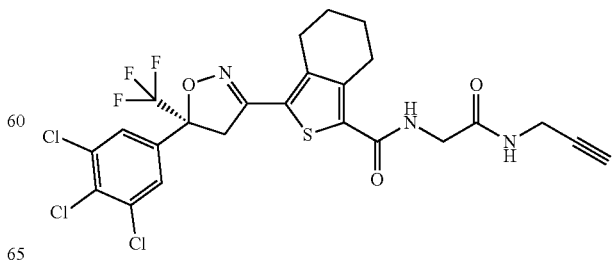

or a salt thereof.

2. A method of controlling sea lice in fish comprising administering to the fish a veterinary effective amount of a compound of the formula:

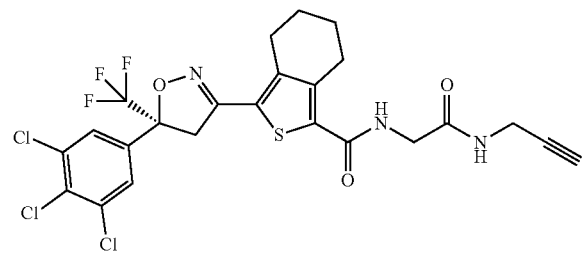 [SMILES: C#CCNC(=O)CNC(=O)c1sc(C2=NO[C@@](c3cc(Cl)c(Cl)c(Cl)c3)(C(F)(F)F)C2)c2c1CCCC2]

or a salt thereof.

3. The method according to claim 2 wherein the fish are salmonids.

4. The method according to claim 2, wherein the compound, or a salt thereof, is orally administered.

5. A medicated fish feed comprising a compound of the formula:

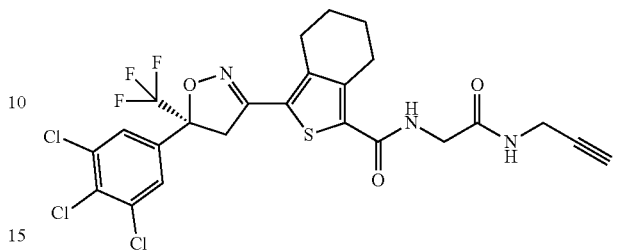

or a salt thereof.

* * * * *